United States Patent
Li et al.

(10) Patent No.: US 9,597,272 B2
(45) Date of Patent: *Mar. 21, 2017

(54) NAIL COMPOSITIONS

(71) Applicant: L'OREAL, Paris (FR)

(72) Inventors: Chunhua Li, Scotch Plains, NJ (US); Ramakrishnan Hariharan, Springfield, NJ (US); Jean-Thierry Simonnet, Mamaroneck, NY (US); Xianzhi Zhou, Leonia, NJ (US); Hy Si Bui, Piscataway, NJ (US); Sarah Fairneny, Garwood, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/649,368

(22) PCT Filed: Dec. 5, 2012

(86) PCT No.: PCT/US2012/067934
§ 371 (c)(1),
(2) Date: Jun. 3, 2015

(87) PCT Pub. No.: WO2014/088570
PCT Pub. Date: Jun. 12, 2014

(65) Prior Publication Data
US 2015/0313831 A1    Nov. 5, 2015

(51) Int. Cl.
*A61K 8/87* (2006.01)
*A61K 8/40* (2006.01)
*A61Q 3/02* (2006.01)
*A61K 8/37* (2006.01)
*A61K 8/58* (2006.01)

(52) U.S. Cl.
CPC .................. *A61K 8/37* (2013.01); *A61K 8/40* (2013.01); *A61K 8/585* (2013.01); *A61K 8/87* (2013.01); *A61Q 3/02* (2013.01); *A61K 2800/30* (2013.01); *A61K 2800/81* (2013.01); *A61K 2800/884* (2013.01); *A61K 2800/95* (2013.01)

(58) Field of Classification Search
CPC ........ A61K 2800/95; A61K 8/37; A61K 8/87; A61Q 3/02
See application file for complete search history.

(56) References Cited

U.S. PATENT DOCUMENTS

| | | |
|---|---|---|
| 5,830,443 A | 11/1998 | Lee |
| 6,000,853 A | 12/1999 | Lytwynec et al. |
| 6,123,931 A | 9/2000 | Ellingson et al. |
| 6,178,639 B1 | 1/2001 | Lytwynec et al. |
| 6,197,316 B1 * | 3/2001 | Ellingson ............... A61K 8/731 424/401 |
| 8,367,742 B2 | 2/2013 | Vu et al. |
| 2011/0060065 A1 * | 3/2011 | Vu ........................ A61K 8/8152 521/149 |
| 2011/0081306 A1 | 4/2011 | Vu et al. |
| 2011/0150805 A1 * | 6/2011 | Kergosien ................ A61K 8/04 424/70.7 |
| 2015/0265524 A1 * | 9/2015 | Li ........................ A61K 8/8117 424/61 |
| 2015/0313831 A1 * | 11/2015 | Li ............................ A61K 8/40 424/61 |

FOREIGN PATENT DOCUMENTS

| | | |
|---|---|---|
| WO | 2011 071795 | 6/2011 |
| WO | 2012 061267 | 5/2012 |

OTHER PUBLICATIONS

International Search Report and Written Opinion of the International Searching Authority Issued Aug. 20, 2013 in PCT/US2012/067934 Filed Dec. 5, 2012.
U.S. Appl. No. 14/649,441, filed Jun. 3, 2015, Li et al.
U.S. Appl. No. 14/416,438, filed Jan. 22, 2015, Li, et al.

* cited by examiner

*Primary Examiner* — Anna Falkowitz
(74) *Attorney, Agent, or Firm* — Oblon, McClelland, Maier & Neustadt, L.L.P.

(57) ABSTRACT

The invention relates to nail composition sets comprising at least one primer, at least one bonding composition, and at least one color coat, wherein the primer comprises water and at least one adhesive compound and preferably further comprises at least one water-soluble film forming agent and/or at least one plasticizer.

16 Claims, 1 Drawing Sheet

| System | Application | Wear 14 days | Remove Procedure Ease of Removal | After Removal Nail Condition |
|---|---|---|---|---|
| Inventive Procedure A (29 Panel) | UV Gel Top Coat / UV Gel Color (2 Coats) / Ultra bonding Agent / Water Based Basecoat (2 Coats) / Nail Surface | ✓✓✓ | Soak nails in warm water or (warm water + surfactant mixture) for 5 minutes, then peal it off. ✓✓✓✓ + | ✓✓✓ |
| Comparative Procedure B (20 Panel) | UV Gel Top Coat / UV Gel Color (2 Coats) / Water Based Basecoat (2 Coats) / Nail Surface | ✓✓ | Soak nails in warm water or (warm water + surfactant mixture) for 5 minutes, then peal it off. ✓✓✓ | ✓✓✓ |
| Comparative Procedure C (29 Panel) | CND Top Coat / CND Colol Coat (2 Coat) / CND Base Coat / Nail Surface / Competitor Product | ✓✓ | Soak finger nails in acetone for 10 minutes, then remove with wooden stick ✓ | ✓ |

NAIL COMPOSITIONS

FIELD OF THE INVENTION

The present invention relates to nail compositions comprising at least one color coat, at least one bonding composition, and at least one primer, wherein the primer comprises water and at least one adhesive compound. The primer preferably further comprises at least one plasticizer. Owing to the primer, such nail compositions can be easily removed with less damage to nails and with more time efficiency.

DISCUSSION OF THE BACKGROUND

Traditional nail enamel can contain a large amount of nitrocellulose, primarily because nitrocellulose provides good adhesion of the compositions to nails upon application. Such conventional nail polish compositions (with or without nitrocellulose) require solvent-based removal products to remove them from nails. However, it is desirable to avoid such solvent-based removers both from a personal perspective (to avoid damage to nails) and an environmental perspective (to avoid damage to the environment).

Other types of nail polish compositions exist. For example, UV (ultraviolet) gel compositions are known. UV gel compositions typically consist of a layer of basecoat for adhesion on the nails, two color coats to enhance the color, and one top coat for shine. Each coating needs to be cured with a UV Lamp or UV LED. A UV gel composition set is a system that contains base coat, color coat and top coat layers. The UV gel composition set's adhesion on the nail and the cohesion among the layers is so strong that it is difficult to remove such compositions from nails. To remove such UV gel products from nails, it is usually required to soak nails with harsh solvent such as acetone for 10 minutes or more to effect removal. Frequent and/or prolonged use of such solvents in this manner can damage nails such as, for example, by making them dry and brittle. At the same time, the removal process can be time-consuming.

In the past, proposed solutions have focused on altering the composition of the UV gel layers themselves by including additives which are soluble in solvents like acetone, ethyl acetate, butyl acetate, etc. to the layers. For instance, US2011082228A, US2011081306A, US2011060065A, US2011182838A, US2011182838A, and US2011274633A relate to the use of a non-reactive, solvent-dissolvable polymer such as cellulose acetate butyrate, cellulose acetate propionate, and mixtures to enhance removal properties. Adding such non-reactive, solvent-dissolvable compounds improves the soaking of the coatings by solvent and hence can speed up the removal process. The speed of removal depends on the type and the quantity of additives introduced in the composition. However, the use of solvent to remove the composition is still required. Moreover, the improvement of nail safety is not perceived.

There remains a need for UV gel compositions which are safe and adhere well to nails, yet which can be easily removed with less damage to nails and with more time efficiency and without sacrificing wear properties.

SUMMARY OF THE INVENTION

The present invention relates to a nail composition set comprising at least one color coat, at least one bonding composition, and at least one primer.

The present invention also relates to a nail composition set comprising (1) at least one color coat, (2) at least one bonding composition, (3) at least one primer, and (4) optionally at least one topcoat and/or at least one basecoat.

The present invention relates to a nail composition set comprising at least one color coat, at least one bonding composition, and at least one primer, wherein the primer comprises water and at least one adhesive compound. The primer preferably further comprises at least one plasticizer and/or coalescent agent.

The present invention also relates to a nail composition set comprising (1) at least one color coat, (2) at least one bonding composition, (3) at least one primer, and (4) optionally at least one topcoat and/or at least one basecoat, wherein the primer comprises water and at least one adhesive compound. The primer preferably further comprises at least one plasticizer and/or coalescent agent.

The present invention further relates to methods for making up and/or protecting nails comprising applying to the nails at least color coat, at least one bonding composition, and at least one primer.

The present invention further relates to methods for making up and/or protecting nails comprising applying to the nails (1) at least one color coat, (2) at least one bonding composition, (3) at least one primer, and (4) optionally at least one topcoat and/or at least one basecoat.

The present invention further relates to methods for making up and/or protecting nails comprising applying to the nails at least one color coat, at least one bonding composition, and at least one primer, wherein the primer comprises water and at least one adhesive compound. The primer preferably further comprises at least one plasticizer and/or coalescent agent.

The present invention further relates to methods for making up and/or protecting nails comprising applying to the nails (1) at least one color coat, (2) at least one bonding composition, (3) at least one primer, and (4) optionally at least one topcoat and/or at least one basecoat, wherein the primer comprises water and at least one adhesive compound. The primer preferably further comprises at least one plasticizer and/or coalescent agent.

The present invention further relates to methods of removing a nail composition set comprising at least one color coat, at least one bonding composition, and at least one primer, wherein the method comprises removing the primer to effect removal of the primer as well as the color coat and the bonding composition of the nail composition.

The present invention further relates to methods of removing a nail composition set comprising (1) at least one color coat, (2) at least one bonding composition, (3) at least one primer, and (4) optionally at least one topcoat and/or at least one basecoat, wherein the method comprises removing the primer to effect removal of the primer as well as the color coat, bonding composition, topcoat and/or basecoat of the nail composition set.

The present invention also relates to a kit for a nail composition set comprising at least one primer composition and at least one bonding composition. Preferably, the kit for a nail composition set further comprise one or more of the following compositions: a topcoat composition; a basecoat composition; a color coat; and/or a UV gel composition. If the kit contains primer but not a basecoat composition, the primer can function as a basecoat in the nail composition set. Preferably, the kit for a nail composition set further comprises instructions for removing a nail composition set by removing the primer composition to effect removal of the nail composition set.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to nails and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

"Adhesion" as used herein, refers to chemical or physical bonding between a coating and a substrate. Good adhesion between nail polish and nail surface should translate to good wear properties on consumers. Adhesion properties can be quantified by in-vitro method such as a cross-cut adhesion test. In the test, a lattice pattern is cut into the coating and penetrates through to the substrate. A pressure sensitive tape is applied to the sample and then pulled off. The adhesion property can be quantified by the area of the coating remaining after peeling. For example, if the whole film remains after peeling, it indicates excellent adhesion. If most of the film gets peeled off, it indicates poor adhesion. The cross-cut test is an industrial standard test for testing adhesion for coatings. (Reference # ISO/DIN 2409, ASTM D3359).

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

The compositions and methods of the present invention can comprise, consist of, or consist essentially of the essential elements and limitations of the invention described herein, as well as any additional or optional ingredients, components, or limitations described herein or otherwise useful.

Nail Composition Set

According to the present invention, a nail composition set comprising at least one color coat, at least one bonding composition, and at least one primer are provided. The nail enamel composition set of the present invention can optionally further comprise at least one basecoat and/or at least one topcoat. "Nail" as used herein includes fingernails as well as toenails.

For example, a nail composition set comprising at least one primer, at least one bonding composition, at least one basecoat, at least one color coat and at least one topcoat are provided. However, the basecoat and/or topcoat are optional. Thus, nail composition sets comprising at least one primer, at least one bonding composition, at least one color coat and at least one top coat, as well as nail composition sets comprising at least one primer, at least one bonding composition, at least one basecoat, and at least one color coat are provided by the present invention.

The nail composition set can also comprise at least one primer, at least one bonding composition, and at least one color coat.

It should be understood that each coat or layer in the nail composition set, itself, can comprise one or more layers of each composition. Thus, the at least one primer can comprise one or more primer layers; the at least one bonding composition can comprise one or more bonding layers; the at least one basecoat can comprise one or more basecoat layers; the at least one color coat can comprise one or more color coat layers; and the at least one topcoat can comprise one or more topcoat layers. Preferably, each primer, bonding composition, basecoat, color coat and topcoat contains three or fewer layers or compositions, more preferably two or fewer layers or compositions, and most preferably a single layer or composition.

According to the present invention, the primer comprises (1) water and (2) water-dispersed latex or psuedolatex. During use, the primer allows an applied nail composition (UV Gel composition) to be easily peeled off.

According to the present invention, the bonding composition comprises (1) organic solvent and (2) at least one adhesive promotion agent. During use, the bonding composition allows an applied nail composition (UV Gel composition) to be adhered to the primer (and, thus, the nail).

According to the present invention, the basecoat, color coat and topcoat of the nail composition set can be any suitable composition for application to nails. For example, the basecoat(s) can be an adhesive layer or an undercoat layer; the color coat(s) can be a nail polish composition(s) such as, for example, a UV gel composition; the topcoat(s) can be a shine layer and/or a protective layer.

During application of the nail composition set, the primer is applied to the nail. Then, the bonding composition is applied to the primer. Then, if used, the basecoat is applied to the bonding composition. Then, the color coat is applied to the basecoat (if used); if basecoat is not used, the color coat is applied to the bonding composition. Then, if used, the topcoat is applied to the color coat. In this manner, a nail composition comprising a primer, a bonding composition, a basecoat (optional), a color coat and a topcoat (optional) can be prepared on a nail.

Alternatively, during application of the nail composition set, the primer is applied to the nail. Then, if used, the basecoat is applied to the primer. Then, the bonding composition is applied to the basecoat. Then, the color coat is applied to the bonding composition. Then, if used, the topcoat is applied to the color coat. In this manner, a nail composition comprising a primer, a basecoat, a bonding composition, a color coat and a topcoat (optional) can be prepared on a nail.

Primer

According to the present invention, a primer composition for application to nails is provided. In accordance with the present invention, the primer comprises (1) water and (2) water-dispersed latex or pseudolatex.

During use, the primer allows a nail composition comprising a nail polish (UV Gel composition) to be easily peeled off. Preferably, the nail composition set can be peeled off in whole pieces.

As explained above, the nail composition set is applied to nail(s) such that the order is nail/primer/basecoat(optional)/bonding composition/color coat/topcoat(optional) or nail/primer/bonding composition/base coat(optional)/color coat/topcoat(optional). During removal, the primer is preferably peeled off from the edge of the nail/nail composition. Such removal of the nail composition is easy and quick (time efficient), and can be performed without the aid of solvent-based removers (although such removers can be used to aid in removal, if desired). The speed of removal of the nail composition can be increased by dipping nail(s) having an applied nail composition into warm water prior to peeling. "Warm water" is defined herein as water above room temperature such as, for example, water at 26° C.-60° C., preferably at 30° C.-50° C., including all ranges and subranges therebetween.

As indicated above, the primer comprises latex or pseudolatex. Latex and pseudolatex are colloidal dispersions of polymer particles in an aqueous liquid phase.

"Latex" is generally obtained by suspension or emulsion polymerization or copolymerization of monomers according to processes that are well known to those of ordinary skill in the art. Such monomers may be chosen in particular from styrene, butadiene, acrylonitrile, chloroprene, vinyl acetate, urethanes, isoprene, isobutylene, and acrylic or methacrylic acid, maleic acid, crotonic acid or itaconic acid or esters or amides thereof.

"Pseudolatex" denotes a dispersion consisting of generally spherical particles of a polymer, these particles being obtained by dispersing the polymer in a suitable aqueous phase.

Latex and pseudolatex have film-forming properties that are advantageous for imparting adhesive properties to the primer. That is, latex and pseudolatex aid in adhering the primer and, thus, the nail composition to the nail.

Specific examples of types of latexes and pseudolatexes as well as specific examples of latexes and pseudolatexes include:

Synthetic polymers of the polycondensate type or of the free-radical type;

Acrylic polymers resulting from the copolymerization of monomers chosen from the esters and/or amides of acrylic acid or of methacrylic acid. As examples of monomers of ester type, mention may be made of methyl methacrylate, ethyl methacrylate, butyl methacrylate, isobutyl methacrylate, 2-ethylhexyl methacrylate and lauryl methacrylate. As examples of monomers of amide type, mention may be made of N-t-butylacrylamide and N-t-octylacrylamide.

Acrylic polymers obtained by copolymerization of ethylenically unsaturated monomers containing hydrophilic groups, preferably of nonionic nature, such as hydroxyethyl acrylate, 2-hydroxypropyl acrylate, hydroxyethyl methacrylate and 2-hydroxypropyl methacrylate;

Vinyl polymers resulting from the homopolymerization or copolymerization of monomers chosen from vinyl esters, styrene or butadiene. As examples of vinyl esters, mention may be made of vinyl acetate, vinyl neodecanoate, vinyl pivalate, vinyl benzoate and vinyl t-butylbenzoate.

Acrylic/Silicone Copolymers;

Polymers resulting from the free-radical polymerization of one or more free-radical monomers inside and/or partially at the surface of preexisting particles of at least one polymer chosen from the group consisting of polyurethanes, polyureas, polyesters, polyesteramides and/or alkyds. These polymers are generally referred to as "hybrid polymers"; and Bimodal film forming agents which form a bimodal interpenetrating network containing multiple functionalities (for example, cationic and anionic functionalities) which is reversibly cross-linked at least partially through the multiple functionalities are disclosed in PCT patent application nos. WO 05/087191 and WO 06/028931, and corresponding U.S. provisional application Nos. 60/551,658, 60/606,985, and 60/627,224, the entire contents of all of which are hereby incorporated by reference in their entirety. Suitable bimodal film forming agents include, but are not limited to, film forming agents having both cationic and anionic functionalities. According to particularly preferred embodiments of the present invention, the bimodal film forming agent comprises at least one acrylic acid-based, (meth)acrylic acid-based, acrylate-based or (meth)acrylate-based monomer having anionic and/or cationic functionalities. Suitable polymers or copolymers include, but are not limited to, polymers comprising polyacrylates such as those identified in the International Cosmetic Ingredient Dictionary and Handbook (9.sup.th ed. 2002) such as, for example, polyacrylate-1, polyacrylate-2, polyacrylate-3, polyacrylate-4 . . . polyacrylate-16, polyacrylate-17, polyacrylate-18, polyacrylate-19 . . . , etc. Such (co)polymers, or similar (co)polymers, can be combined individually or with other (co)polymers in such a way to form suitable bimodal film forming agents having both cationic and anionic functionalities. According to particularly preferred embodiments, the bimodal film forming agent is selected from the group consisting of polymers consisting of polyacrylate-21 and acrylates/dimethylaminoethylmethacrylate copolymer (marketed under the name Syntran PC 5100 by Interpolymer), polyacrylate-16 (marketed under the name Syntran PC 5112 by Interpolymer), polyacrylate-18 and polyacrylate-19 (marketed under the name Syntran PC 5107 by Interpolymer), and polyacrylate-18 and polyacrylate-1 g (marketed under the name Syntran PC 5117 by Interpolymer). The bimodal film forming agent containing polyacrylate-21 and acrylates/dimethylaminoethylmethacrylate copolymer (Syntran PC 5100) and polyacrylate-16 (Syntran PC 5112) are particularly preferred.

Representative examples of suitable latexes include acrylic copolymer dispersions sold under the names Neocryl XK-90® (INCI name: acrylic/styrene copolymer), Neocryl A-1070® (INCI name: acrylic/styrene copolymer), Neocryl A-1090® (INCI name: acrylic/styrene copolymer), Neocryl BT-62® (INCI name: acrylic/styrene copolymer), Neocryl A-1079® (INCI name: acrylic/styrene copolymer) and Neocryl A-523® (INCI name: acrylic/styrene copolymer) by the company Avecia-Neoresins, Dow Latex 432® (INCI name: Styrene/Acrylates Copolymer) by the company Dow Chemical, Daitosol 5000 AD® (INCI name: acrylates copolymer) by the company Daito Kasey Kogyo; or the aqueous dispersions of polyurethane sold under the names Neorez R-981® (INCI name: polyester-polyurethane copolymer) and Neorez R-974® (INCI name: polyester-polyurethane copolymer) by the company Avecia-Neoresins, Avalure UR-405® (INCI name: polyurethane-2), Avalure UR-410® (INCI name: polyurethane-2), Avalure UR-425° (INCI name: polyurethane-2), Avalure UR-450® (INCI name: PPG-17/IPDI/DMPA copolymer), Sancure 875® (INCI name: polyester-polyurethane copolymer), Sancure 861® (INCI name: polyester-polyurethane copolymer), Sancure 878® (INCI name: polyester-polyurethane copolymer) and Sancure 2060° (INCI name: polyester-polyurethane copolymer) by the company Goodrich, Impranil 85® (INCI name: Water and Polyurethane/Polyester) by the company Bayer and Aquamere H-1511® (INCI name: PVP/polycarbamyl/polyglycol Ester) by the company Hydromer.

Further examples of latex polymers useful in the present invention include (meth)acrylate copolymers such as, for example, acrylate copolymers (acrylates/ethylhexyl acrylate copolymer, sold by Daito Kasei under the tradename Daitosol 5000SJ), butyl acrylate/hydroxypropyl dimethicone acrylate copolymers (Granacrysil BAS by Grant Industries, Inc.), acrylates/C12-C22 alkylmethacrylate copolymers (Allianz OPT by ISP), isododecane and acrylates copolymers (Giovarez AC-5099M by Phoenix), and acrylates/octylacrylamide copolymers (Dermacryl-79 by National Starch & Chemical Company).

Still further examples of suitable latexes include those disclosed in U.S. Pat. No. 7,445,770 and/or U.S. Pat. No. 7,452,770, the entire contents of both of which are hereby incorporated by reference. For example, suitable latexes include aqueous polyurethane dispersions including the reaction products of:

A) a prepolymer according to the formula:

wherein $R_1$ represents a bivalent radical of a dihydroxyl functional compound, $R_2$ represents a hydrocarbon radical of an aliphatic or cycloaliphatic polyisocyanate, $R_3$ represents a radical of a low molecular weight diol, optionally substituted with ionic groups, n is from 0 to 5, and m is >1;

B) at least one chain extender according to the formula: $H_2N—R_4—NH_2$ wherein $R_4$ represents an alkylene or alkylene oxide radical not substituted with ionic or potentially ionic groups; and C) at least one chain extender according to the formula: $H_2N—R_5—NH_2$ wherein $R_5$ represents an alkylene radical substituted with ionic or potentially ionic groups.

Suitable dihydroxyl compounds for providing the bivalent radical $R_1$ include those having two hydroxy groups and having number average molecular weights of from about 700 to about 16,000, and preferably from about 750 to about 5000. Examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. The polyester polyols, polyether polyols and polyhydroxy polycarbonates are preferred. Mixtures of various such compounds are also within the scope of the present invention.

Suitable polyisocyanates for providing the hydrocarbon radical $R_2$ include organic diisocyanates having a molecular weight of from about 112 to 1,000, and preferably from about 140 to 400. Preferred diisocyanates are those represented by the general formula $R_2(NCO)_2$ indicated above in which $R_2$ represents a divalent aliphatic hydrocarbon group having from 4 to 18 carbon atoms, a divalent cycloaliphatic hydrocarbon group having from 5 to 15 carbon atoms, a divalent araliphatic hydrocarbon group having from 7 to 15 carbon atoms or a divalent aromatic hydrocarbon group having 6-15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanato naphthalene. Mixtures of diisocyanates can, of course, be used. Preferred diisocyanates are aliphatic and cycloaliphatic diisocyanates. Particularly preferred are 1,6-hexamethylene diisocyanate and isophorone diisocyanate.

"Low molecular weight diols" in the context of $R_3$ means diols having a molecular weight from about 62 to 700, preferably 62 to 200. They may contain aliphatic, alicyclic or aromatic groups. Preferred compounds contain only aliphatic groups. The low molecular weight diols having up to about 20 carbon atoms per molecule include ethylene glycol, diethylene glycol, propane 1,2-diol, propane 1,3-diol, butane 1,4-diol, butylene 1,3-glycol, neopentyl glycol, butyl ethyl propane diol, cyclohexane diol, 1,4-cyclohexane dimethanol, hexane 1,6-diol, bisphenol A (2,2-bis(4-hydroxyphenyl) propane), hydrogenated bisphenol A (2,2-bis(4-hydroxycyclohexyl)propane), and mixtures thereof. Optionally, the low molecular weight diols may contain ionic or potentially ionic groups. Suitable lower molecular weight diols containing ionic or potentially ionic groups are those disclosed in U.S. Pat. No. 3,412,054, the contents of which is hereby incorporated by reference. Preferred compounds include dimethylol butanoic acid (DMBA), dimethylol propionic acid (DMBA) and carboxyl-containing caprolactone polyester diol. If lower molecular weight diols containing ionic or potentially ionic groups are used, they are preferably used in an amount such that <0.30 meq of COOH per gram of polyurethane in the polyurethane dispersion are present.

The prepolymer is chain extended using two classes of chain extenders. First, compounds having the formula: $H_2N—R_4—NH_2$ wherein $R_4$ represents an alkylene or alkylene oxide radical not substituted with ionic or potentially ionic groups. Alkylene diamines include hydrazine, ethylenediamine, propylenediamine, 1,4-butylenediamine and piperazine. The alkylene oxide diamines include 3-{2-[2-(3-aminopropoxyl)ethoxy]ethoxy}propylamine (also known as dipropylamine diethyleneglycol or DPA-DEG available from Tomah Products, Milton, Wis.), 2-methyl-1,5-pentanediamine (Dytec A from DuPont), hexane diamine, isophorone diamine, and 4,4-methylenedi-(cyclohexylamine), and the DPA-series ether amines available from Tomah Products, Milton, Wis., including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used.

The second class of chain extenders are compounds having the formula: $H_2N-R_5-NH_2$ wherein $R_5$ represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be selected from the group consisting of ternary or quaternary ammonium groups, groups convertible into such a group, a carboxyl group, a carboxylate group, a sulfonic acid group and a sulfonate group. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid (AAS) or the sodium salt of N-(2-aminoethyl)-2-aminopropionic acid.

Commercially available examples of such latexes include, but are not limited to, aqueous polyurethane dispersions comprising a reaction product of a prepolymer comprising a dihydroxyl compound, a polyisocyanate, and a low molecular weight diol and at least two diamine compounds and wherein the composition is substantially free of triethanolamine stearate such as, for example, those sold under the BAYCUSAN® name by Bayer such as, for example, BAYCUSAN® C1000 (polyurethane-34), BAYCUSAN® C1001 (polyurethane-34), BAYCUSAN® C1003 (polyurethane-32), and BAYCUSAN® C1004 (polyurethane-35).

Finally, suitable examples of latexes/pseudolatexes can be found, for example, in U.S. patent application Ser. Nos. 61/541,173, 61/542,131, and 61/542,136, U.S. patent application publication no. 2008/0081054, and U.S. Pat. Nos. 5,538,717, 5,672,647, 6,297,950 and 6,372,201, the entire contents of all of which are hereby incorporated by reference.

Preferably, the latex or pseudolatex is present in the inventive primer compositions in amounts of active material generally ranging from about 5% to about 50%, more preferably from about 10% to about 45%, and more preferably from about 20% to about 40%, by weight, based on the total weight of the composition, including all ranges and subranges in between Preferably, total water content present in the inventive primer compositions is in amounts generally ranging from about 10% to about 95%, more preferably from about 25% to about 70%, and more preferably from about 30% to about 65%, by weight, based on the total weight of the composition, including all ranges and subranges in between. According to preferred embodiments, the primer is "water-based," meaning that the continuous phase is water.

According to particularly preferred embodiments of the present invention, the primer composition further comprises one or more ingredients selected from the group consisting of water-soluble film forming agents, coalescent agents and plasticizers.

According to particularly preferred embodiments of the present application, compositions further comprising at least one water-soluble film forming agent are provided. A "water-soluble film forming agent" is a polymer which can be dissolved in an aqueous phase.

Specific examples of suitable water-soluble film forming agents include, but are not limited to, proteins, such as proteins of plant origin, such as, for example, wheat or soya proteins; or proteins of animal origin, such as keratins, for example keratin hydrolysates and sulfonic keratins; cellulose polymers, such as, for example, hydroxyethylcellulose, hydroxypropylcellulose, methylcellulose or ethylhydroxyethylcellulose; acrylic polymers or copolymers, such as, for example, polyacrylates or polymethacrylates; vinyl polymers, such as, for example, polyvinylpyrrolidones, copolymers of methyl vinyl ether and of maleic anhydride, the copolymer of vinyl acetate and of crotonic acid, copolymers of vinylpyrrolidone and of vinyl acetate, copolymers of vinylpyrrolidone and of caprolactam, or polyvinyl alcohol; gums arabic, guar gum, xanthan derivatives or karaya gum; alginates and carrageenans; glycoaminoglycans, hyaluronic acid and its derivatives; shellac resin, gum sandarac, dammars, elemis or copals; muccopolysaccharides, such as chondroitin sulfates; and their mixtures.

According to preferred embodiments, the at least one water-soluble film forming agent, if present, is present in the compositions of the present invention in an amount of active material ranging from about 0.01 to about 30% by weight, more preferably from about 0.1 to about 20% by weight, and most preferably from about 1 to about 10% by weight, based on the total weight of the composition, including all ranges and subranges within these ranges.

According to particularly preferred embodiments of the present application, primer compositions further comprising at least one plasticizer and/or coalescent are provided. Plasticizers are additives used to optimize the mechanical properties of the films. They tend to reduce the Glass Transition Temperature (Tg) and increase the softness and flexibility of the films. Coalescents are additives used to aid the coalescence of the latex particles, and hence assisting the film formation process.

Preferably, the plasticizer has a distribution coefficient D of less than or equal to 0.1. The distribution coefficient can be determined in accordance with the teaching of "A method to predict the distribution coefficient of coalescing agents between latex particles and the water phase," *Progress in Organic Coatings*, vol. 30, 1997, pp. 173-177, the disclosure of which is specifically incorporated by reference herein.

Preferably, the plasticizer has a boiling point measured at ambient pressure of less than or equal to 285° C., preferably less than or equal to 270° C., and preferably less than or equal to 250° C. In the present specification, the boiling point values are to be considered accurate to ±2° C. owing to the uncertainties of boiling point measurement.

Any plasticizing agent typically found in nail polish compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of teributyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, and mixtures thereof.

In accordance with preferred embodiments, the plasticizer, if present, is preferably present in the primer composition in an amount of from 0.1% to 25% by weight, preferably from 0.25% to 22% by weight, preferably from 0.5 to 20% by weight, of the total weight of the composition, including all ranges and subranges therebetween.

According to particularly preferred embodiments of the present application, primer compositions further comprising at least one coalescent agent are provided. The coalescent agent promotes the coalescence of the polymer(s) in the composition.

Preferably, the coalescent agent has a distribution coefficient D' of greater than or equal to 0.5, measured in accordance with the above-referenced "A method to predict the distribution coefficient of coalescing agents between latex particles and the water phase," *Progress in Organic Coatings*, vol. 30, 1997, pp. 173-177.

Preferably, the coalescent agent has a boiling point measured at ambient pressure ranging from 90° C. to 180° C., preferably from 150° C. to 180° C.

Any coalescent agent typically found in nail polish compositions can be used. Examples of suitable plasticizers include, but are not limited to, propylene glycol n-butyl ether, dipropylene glycol dimethyl ether, propylene glycol methyl ether acetate, propylene glycol propyl ether, methyl lactate, ethyl lactate, isopropyl lactate, and mixtures thereof.

In accordance with preferred embodiments, the coalescent agent, if present, is preferably present in the primer composition in an amount of from 0.1% to 25% by weight, preferably from 1% to 15% by weight, preferably from 3 to 10% by weight, of the total weight of the composition, including all ranges and subranges therebetween.

Bonding Composition

According to the present invention, a bonding composition for application to nails is provided. In accordance with the present invention, the bonding composition comprises (1) solvent; and (2) adhesive promotion agent. According to preferred embodiments of the present invention, the bonding composition is applied to the primer composition such that it does not cover the entirety of the primer composition coat or layer previously applied to the nails. For example, after application of the primer composition such that it covers the entire nail, the bonding composition can be applied only to the outside edge or circumference of the nail, thereby leading to application of the bonding composition along the outside edges (or any portion thereof such as the fingernail tip) of the applied primer composition. However, such circumferential application is not required for purposes of the present invention. Rather, the bonding composition can be applied over any portion of the primer composition coat or layer previously applied to the nails, up to and including application over the entire primer composition coat or layer.

Suitable solvents for the bonding composition include any solvent typically found in nail polish compositions. Preferably, the solvent is an organic solvent. Also preferably, the solvent has a boiling point lower than 80° C., preferably lower than 75° C., preferably lower than 70° C., and preferably lower than 65° C. Suitable solvents include, but are not limited to, organic solvents which are liquid at ambient temperature. Examples of suitable solvents include, but are not limited to, ketones such as methyl ethyl ketone, methyl isobutyl ketone, diisobutyl ketone, isophorone, cyclohexanone or acetone; alcohols, such as ethanol, isopropanol, diacetone alcohol, 2-butoxyethanol or cyclohexanol; glycols, such as ethylene glycol, propylene glycol, pentylene glycol or glycerol; propylene glycol ethers, such as propylene glycol monomethyl ether, propylene glycol monomethyl ether acetate or dipropylene glycol mono(n-butyl) ether; short-chain esters (having a total of 2 to 7 carbon atoms), such as ethyl acetate, methyl acetate, propyl acetate, n-butyl acetate or isopentyl acetate; alkanes, such as decane, heptane, dodecane or cyclohexane; and their mixtures. Most preferred are short-chain esters (having a total of from 2 to 8 carbon atoms).

In accordance with preferred embodiments, the majority (that is, greater than 50%) of the bonding composition is solvent. Preferably, the solvent is present in the composition in an amount of from 51% to 90% by weight, preferably from 60% to 85% by weight, preferably from 70 to 85% by weight, of the total weight of the composition, including all ranges and subranges therebetween.

Suitable adhesive promotion agents include those forming an adhesive film without the need for photocuring by UV exposure. Preferably, the adhesive promotion agent has a molecular weight of 5,000 or lower, preferably 3,000 or lower, preferably 2,500 or lower, and preferably 2,000 or lower. If desired, the adhesive promotion agents may be covalently attached to supports such as polymers, oligomers or dendrimers, with the polymer or oligomer being linear, branched, comb or block, and the distribution of agents being random, terminal or form block.

Suitable adhesive promotion agents include, but are not limited to, acrylic and/or methacrylic ("(meth)acrylic") monomers and/or oligomers, urethanes, alkoxysilanes, and cyanoacrylates.

Suitable (meth)acrylic monomers and/or oligomers are disclosed in US Ser. Nos. 61/476,340, 61/476,338, 61/476,337, 61/476,339, 61/476,341 and PCT/US12/40724 as well as in U.S. Pat. Nos. 6,244,274, 5,785,958, 6,391,938, 6,803,394, 5,965,147, 6,0155,549 and US patent applications 2011/0081306, 2011/0060065, 2011/182838, 2011/274633, the entire contents of all of which are hereby incorporated by reference. Preferably, (meth)acrylic "oligomers" contain 10 or fewer monomers, preferably 7 or fewer monomers, preferably 5 or fewer monomers, and preferably 4 or fewer monomers.

Suitable alkoxysilanes include, but are not limited to, silanes having one alkoxylated substituent, silanes having two alkoxylated substituents, silanes having three alkoxylated substitutents, and silanes having four alkoxylated substituents. Preferably, the alkoxylated groups contain between 1 and 10 carbon atoms, preferably between 1 and 5 carbon atoms, preferably between 1 and 3 carbon atoms, including all ranges and subranges therebetween. Preferably, the alkoxylated groups are unsubstituted. However, it is possible for the alkoxylated groups to contain substitutions such as, for example, nitrogen-containing compounds (amino, amido). Particularly preferred alkoxylated silanes include:

| Chemical Name | | Structure |
|---|---|---|
| APTES | (3-Aminopropyl)-triethoxysilane |  |
| TEOS | Tetraethyl orthosilicate |  |
| MTES | Methyltriethoxysilane |  |
| DMDES | Dimethyldimethoxysilane |  |

Suitable cyanoacrylates include alkyl cyanoacrylates and alkoxy cyanoacrylates. Preferably, for alkyl cyanoacrylates, the alkyl group(s) contains 1-10 carbon atoms, preferably 1-6 carbon atoms, and preferably 1-4 carbon atoms, including all ranges and subranges therebetween. Preferably, for alkoxy cyanoacrylates, the alkoxy group(s) contains 1-5 carbon atoms, preferably 1-4 carbon atoms, and preferably 1-3 carbon atoms, including all ranges and subranges therebetween. Specific example of suitable cyanoacrylates include 2-ethyl cyanoacrylate, 2-cyanoacrylate, methyl 2-cyanoacrylate, n-propyl 2-cyanoacrylate, isopropyl 2-tert-butyl cyanoacrylate, 2-cyanoacrylate, n-butyl 2-cyanoacrylate, isobutyl 3-methoxybutyl cyanoacrylate, cyanoacrylate, n-decyl 2-cyanoacrylate, hexyl 2-cyanoacrylate, 2-ethoxyethyl 2-cyanoacrylate, 2-methoxyethyl 2-cyanoacrylate, 2-octyl 2-cyanoacrylate, 2-propoxyethyl 2-cyanoacrylate, n-octyl cyanoacrylate and isoamyl cyanoacrylate.

Preferred cyanoacrylates include those of the formula (including mixtures thereof):

wherein:
$Z=-(CH_2)_7-H_3$,
$-CH(CH_3)-(CH_2)_5-CH_3$,
$-CH_2-CH(C_2H_5)-(CH_2)_3-CH_3$,
$-(CH_2)_5-CH(CH_3)-CH_3$,
$-(CH_2)_4-CH(C_2H_5)-CH_3$.

Suitable cyanoacrylates can also be found in U.S. Pat. Nos. 3,840,490 and 4,844,102, as well as US patent application 2011/0048440, the entire contents of all of which are hereby incorporated by reference.

In accordance with preferred embodiments, the adhesive promotion agent is present in the composition in an amount of from 3% to 49% by weight, preferably from 4% to 40% by weight, preferably from 5 to 20% by weight, of the total weight of the composition, including all ranges and subranges therebetween.

Color Coat

According to the present invention, a color coat for application to nails is provided. In accordance with the present invention, the color coat comprises at least one colorant. Any colorant typically found in nail polish compositions can be used. Suitable colorants include, but are not limited to, lipophilic dyes, pigments and pearlescent agents, and their mixtures.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

In accordance with preferred embodiments, the colorant is preferably present in the color coat in an amount of from 0.01% to 20% by weight, preferably from 0.1% to 15% by weight, preferably from 0.5 to 10% by weight, of the total weight of the composition, including all ranges and subranges therebetween.

The color coat is a UV gel nail composition. Examples of suitable UV gel nail compositions can be found, for example, in U.S. Pat. Nos. 5,435,994, and 5,456,905, and US patent application publication nos. 2011/082228, 2011/081306, 2011/060065, 2011/182838, 2011/274633. Further, suitable compositions can be found in U.S. Ser. No. 61/476,339, the entire contents of which is hereby incorporated by reference in its entirety.

Topcoat/Basecoat

According to preferred embodiments of the invention nail composition sets, these sets can further contain at least one basecoat and/or at least one topcoat. The basecoat and topcoat are optional in the nail composition set of the present invention. However, it is preferred if both coats are present. In accordance with these preferred embodiments, any topcoat suitable for application to nails as a topcoat and any basecoat suitable for application to nails as a basecoat can be used. That is, the topcoat and basecoat employed in the nail compositions of the present invention is not limited: as long as the topcoat and basecoat are suitable for application to nails, they are suitable for the nail composition set of the present invention. Typically, topcoats provide shine and/or protection to color coats of nail composition set, and basecoats provide adhesion of the color coat to the nail (or, in the case of the present invention, the primer)

Auxiliaries/Additives

The primer, the basecoat, the color coat, and the topcoat of the layers in the nail composition set of the present invention may additionally comprise an additive or auxiliary commonly used in cosmetic compositions and known to a person skilled in the art as being capable of being incorporated into a nail polish or varnish composition. Such additives or auxiliaries may be chosen from thickeners, coalescents, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable. The composition may be in any galenic form normally employed in the cosmetic and dermatological fields which is suitable for topical administration onto nails.

According to preferred embodiments of the present invention, methods of making up or protecting nails comprising applying to the nails at least one primer, at least one bonding composition, and at least one color coat to nails in an amount sufficient to makeup or protect the nails are provided. According to preferred embodiments, at least one basecoat and/or at least one topcoat are further applied to the nails in the following order: nail/primer/basecoat(if applied)/bonding composition/color coat/topcoat(if applied) or nail/primer/bonding composition/basecoat (if applied)/color coat/topcoat (if applied).

According to preferred embodiments of the present invention, methods for making up and/or protecting nails comprising applying to the nails at least one primer and at least one color coat, wherein the primer comprises water and at least one latex or pseudolatex, in an amount sufficient to makeup or protect the nails are provided. The primer preferably further comprises at least one water-soluble film forming agent and/or at least one plasticizer and/or at least one coalescent agent. According to preferred embodiments, at least one basecoat and/or at least one topcoat are further applied to the nails in the following order: nail/primer/basecoat(if applied)/bonding composition/color coat/topcoat (if applied) or nail/primer/bonding composition/basecoat (if applied)/color coat/topcoat (if applied).

"Making up" as used herein means to provide decoration (for example, color) to the nail. "Protecting" as used herein means to inhibit damage to the nail (for example, chipping) by providing a protective layer on the nail.

In accordance with preferred embodiments of the preceding methods, at least one primer, at least one bonding composition, and at least one color coat are applied topically to the nails of a person in need of (desirous) the desired making up or protection in an amount sufficient to achieve the desired result. The compositions may be applied to the desired area as needed.

According to preferred embodiments, methods of removing a nail composition comprising (1) one or more of: a topcoat; a color coat; and a basecoat, (2) a bonding composition; and (3) at least one primer, wherein the method comprises removing the primer to effect removal of the primer as well as the bonding composition, topcoat, color coat and/or basecoat of the nail composition are provided.

According to preferred embodiments of the present invention, a kit for a nail composition set comprising at least one primer composition and at least one bonding composition composition are also provided. Preferably, the kit further comprises one or more of the following compositions: a topcoat composition; a basecoat composition; a color coat composition; and/or a UV gel composition. Preferably, the kit further comprise instructions for removing a nail composition by removing the primer composition to effect removal of the nail composition.

The compositions according to the invention can be manufactured by known processes used generally in the cosmetics or dermatological field.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1

Exemplary Compositions

| INCI Name | Water-based Basecoat RM % | Bonding composition % | UV gel Color Coat % | UV Gel Base/Top Gel % |
|---|---|---|---|---|
| Di-Hema Trimethylhexyl Dicarbamate* | | | 50 to 65 | 50 to 60 |
| HEMA | | | 5 to 10 | 15 to 20 |
| Hydroxypropyl methacrylate | | | 5 to 10 | 15 to 20 |
| Isobornyl methacrylate | | | — | — |
| Hydroxycyclohexyl phenyl ketone | | | 1 to 2 | 0 to 1 |
| Trimethylbenzoyl Diphenylphosphine Oxide | | | 0 to 1 | 0 to 1 |
| Violet 2/CI 60725 | | | — | 0 to 1 |
| PEG-9 Dimethacrylate | | | 1 to 7 | — |
| Ethyl Acetate | | 80-85 | — | — |
| Acrylic acid2,2-bis-(4-(2-hydroxy-3-methacryloxypropoxy)BISGMA | | 5 to 10 | — | — |
| HEMA | | 5 to 10 | | |
| STYRENE/ACRYLATES/AMMONIUM METHACRYLATE COPOLYMER (and) SODIUM LAURYL SULFATE (and) SODIUM LAURETH SULFATE | 61 | | | |
| AMMONIUM ACRYLATES COPOLYMER | 22 | | | |
| STYRENE/ACRYLATES COPOLYMER | 5.32 | | | |
| POLYURETHANE-34 | 2.85 | | | |
| DIPROPYLENE GLYCOL MONOBUTYL ETHER | 1 | | | |
| Propylene Glycol Dibenzoate | 4.59 | | | |
| TRIBUTYL CITRATE | 1.24 | | | |
| Phenoxyethanol | 1 | | | |
| Caprylyl Glycol | 1 | | | |

Example 2

Exemplary Methods of Application

| Inventive procedure A | Comparative procedure B | Comparative procedure C (Commercial Product CND) |
|---|---|---|
| UV Gel Top Coat | | |
| UV Gel Color Coat 2 | UV Gel Top Coat | CND Top Coat |
| UV Gel Color Coat 1 | UV Gel Color Coat 2 | CND Color Coat 2 |
| Ultra-Bonding Agent | UV Gel Color Coat 1 | CND Color Coat 1 |
| Water-Based Base Coat (1 or 2 Coats) | Water-Based Base Coat (1 or 2 Coats) | CND Basecoat |
| Nail Surface | Nail Surface | Nail Surface |

Example 3

Application of inventive procedure A in example 2.

| Step | Order | Inventive Procedure A - Application Instructions |
|---|---|---|
| PREP | 1 | Wipe nails with Alcohol wipes |
| Water-Based Basecoat | 2 | Apply 1 layer of the water-based basecoat let dry for 1 min (DO NOT CURE) |
| | 3 | Apply 2nd layer of the water-based basecoat (Optional) let dry for 1 min (DO NOT CURE) |
| Bonding composition | 4 | Apply System bonding composition to the free edge of the nail plate Let dry for 30 s (DO NOT CURE) |
| COLOR | 5 | Apply UV gel Color Coat (from above table) in thin layer Cure for 30 s with LED Lamp |
| | 6 | Apply 2nd coat of UV gel Color Coat (from above table) in thin layer Cure for 30 s with LED Lamp |

Example 4

Application of Comparative procedure B in example 2.

| Step | Order | Comparative Procedure B - Application Instructions |
|---|---|---|
| PREP | 1 | Wipe nails with Alcohol wipes |
| Water- Based Basecoat | 2 | Apply 1 layer of the water-based basecoat let dry for 1 min (DO NOT CURE) |
| | 3 | Apply 2nd layer of the water-based basecoat (Optional) let dry for 1 min (DO NOT CURE) |
| COLOR | 4 | Apply UV gel Color Coat (from above table) in thin layer Cure for 30 s with LED Lamp |
| | 5 | Apply 2nd coat of UV gel Color Coat (from above table) in thin layer Cure for 30 s with LED Lamp |
| TOP | 6 | Apply UV gel Top Coat (from above table) in thin layer and cap free edge Cure for 1 min with LED Lamp |
| STICKY LAYER REMOVAL | 7 | Use the Alcohol wipes provided to wipe the nail and remove the tacky layer |

Example 5

Application of Comparative procedure C in example 2.

| Step | Order | Comparative C - CND Application Instructions |
|---|---|---|
| PREP | 1 | Wipe nails with Alcohol wipes |
| BASE | 3 | Shake the bottle of CND BASE Apply CND BASE in thin layer and cap free edge Cure for 10 s with UV Lamp |
| COLOR | 4 | Shake the bottle of CND Color Apply CND COLOR in thin layer and cap free edge Cure for 2 min with UV Lamp |
| | 5 | Apply 2nd coat of CND COLOR in thin layer and cap free edge Cure for 2 min with UV Lamp |
| TOP | 6 | Apply CND TOP in thin layer and cap free edge Cure for 2 min with UV Lamp |
| STICKY LAYER REMOVAL | 7 | Use the Alcohol wipes provided to wipe the nail and remove the tacky layer |

(Continued from previous column:)

| Step | Order | Inventive Procedure A - Application Instructions |
|---|---|---|
| TOP | 7 | Apply UV gel Top Coat (from above table) in thin layer and cap free edge Cure for 1 min with LED Lamp |
| STICKY LAYER REMOVAL | 8 | Use the Alcohol wipes provided to wipe the nail and remove the tacky layer |

Example 6

Removal Instructions for products applied in examples 3 and 4.

| Order | Removal Instructions for Inventive Procedure A and Comparative Procedure B |
|---|---|
| 1 | Soak hands in (warm water (40 C.) or Warm water plus surfactant mixture) for 5 min |
| 2 | Find the edge of the nail polish layer (near cuticle or free edge, whichever easier) and peel the film off the nail For films that are not easily peeled off, whenever it is necessary, use the cuticle pusher to assist the removal process Re-Dip the nails in remover as necessary to aide in removal |
| 3 | Apply cuticle oil |

Example 7

Removal Instructions for products applied in example 5.

| Step | Order | Removal Instructions for CND |
|---|---|---|
| Soak | 1 | Soak cotton swab in Acetone and place on nail Wrap the cotton swab and nail with foil |
| Wait | 2 | Check after 10 minutes and then remove foil |
| Finish | 3 | Use orangewood stick to push any remaining polish off nail |
| Care | 4 | Apply cuticle oil |

Example 8

Figure 1:
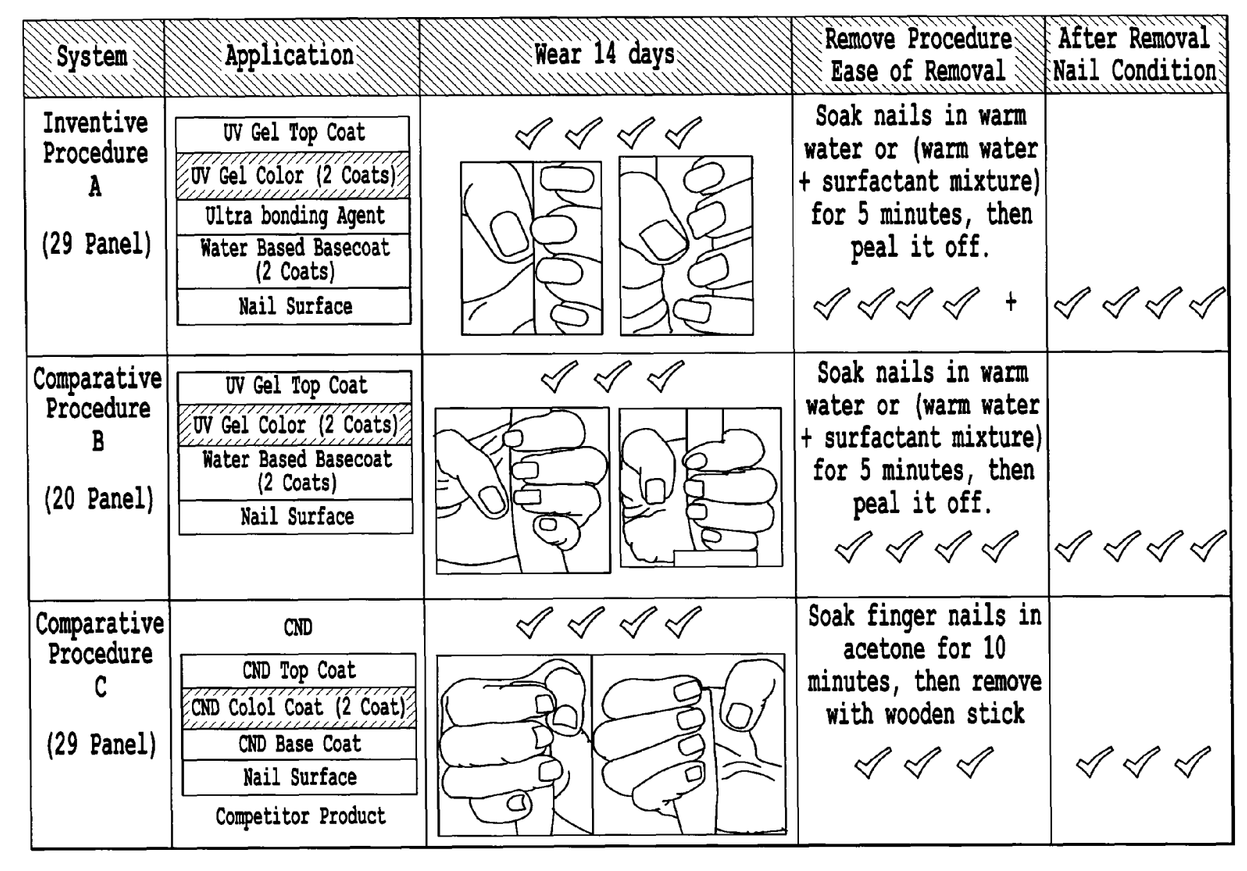
FIG. 1 is a table summarizing the results in the examples and demonstrating poor wear (chipping) of the nails treated in accordance with comparative procedure B and the poor nail condition after treatment in accordance with comparative procedure C.

Inventive procedure A and comparative procedures B and C were performed (as described above) on consumer panels by professional manicurists. Wear was monitored at 7 days and 14 days. Removal occurred at 14 days. It was observed by the manicurists that the inventive procedure including the bonding composition resulted in improved wear properties as compared to the comparative procedures, particularly at the tip of the nails (outer edges of the nails). Further, both manicurists and consumer panelists noted that inventive procedure A resulted in much easier removal properties than comparative procedure C, and left the nail in healthier condition than the acetone removal properties of comparative composition C The inventive procedure A was noted to be clean, fast, easier and healthier for nails, and much preferred over traditional acetone removal processes. Results are summarized in FIG. 1.

What is claimed is:

1. A nail composition set comprising at least one primer that comprises (a) water and (b) at least one latex and/or at least one pseudolatex, at least one bonding composition, and at least one color coat; wherein the least one latex and/or at least one pseudolatex comprises at least one aqueous polyurethane dispersion comprising a reaction product of:

a prepolymer according to the following formula:

wherein $R_1$ represents a dihydroxyl compound having a number average molecular weights of from about 700 to about 16,000, $R_2$ represents a hydrocarbon radical of an aliphatic or cycloaliphatic polyisocyanate, and $R_3$ represents a radical of a low molecular weight diol, n is from 0 to 5, and m is >1;

at least one chain extender according to the formula: $H_2N$—$R_4$—$NH_2$ wherein $R_4$ represents an alkylene or alkylene oxide radical not substituted with ionic or potentially ionic groups; and at least one chain extender according to the formula: $H_2N$—$R_5$—$NH_2$ wherein $R_5$ represents an alkylene radical substituted with ionic or potentially ionic groups.

2. The nail composition set of claim 1, further comprising at least one basecoat and/or at least one topcoat.

3. The nail composition set of claim 1, wherein the color coat is a UV gel composition.

4. The nail composition set of claim 1, wherein the at least one aqueous polyurethane dispersion comprises a reaction product of a prepolymer comprising a dihydroxyl compound, a polyisocyanate, and a low molecular weight diol and at least two diamine compounds and wherein the composition is substantially free of triethanolamine stearate.

5. The nail composition set of claim 1, wherein the primer further comprises at least one water-soluble film forming agent.

6. The nail composition set of claim 1, wherein the primer further comprises at least one plasticizer.

7. The nail composition set of claim 1, wherein the color coat comprises at least one colorant.

8. The nail composition set of claim 1, wherein the primer is water-based.

9. The nail composition set of claim 1, wherein the bonding composition comprises at least one organic solvent and at least one adhesive promotion agent selected from the group consisting of (meth)acrylic monomers and/or oligomers, urethanes, alkoxysilanes, and cyanoacrylates.

10. The nail composition set of claim 1, wherein the bonding composition comprises 51%-90% by weight of organic solvent prior to application to the nail.

11. The nail composition set of claim 1, wherein the bonding composition comprises less than 40% by weight of adhesive promotion agent prior to application to the nail.

12. A method of removing a nail composition set comprising at least one color coat, at least one bonding composition, and at least one primer that comprises (a) water and (b) at lean one latex and/or at least one pseudolatex, comprising removing the primer from a nail to effect removal of the primer as well as the color coat and the bonding composition of the nail composition set; wherein the least one latex and/or at least one pseudolatex comprises at least one aqueous polyurethane dispersion comprising a reaction product of:

a prepolymer according to the following formula:

wherein $R_1$ represents a dihydroxyl compound having a number average molecular weights of from about 700 to about 16,000, $R_2$ represents a hydrocarbon radical of an aliphatic or cycloaliphatic polyisocyanate, and $R_3$ represents a radical of a low molecular weight diol, n is from 0 to 5, and m is >1;

at least one chain extender according to the formula: $H_2N$—$R_4$—$NH_2$ wherein $R_4$ represents an alkylene or alkylene oxide radical not substituted with ionic or potentially ionic groups; and at least one chain extender according to the formula: $H_2N$—$R_5$—$NH_2$ wherein $R_5$ represents an alkylene radical substituted with ionic or potentially ionic groups.

13. The method of claim 12, wherein the color coat is a UV gel composition.

14. A kit for a nail composition set comprising (a) at least one primer composition comprising (i) water and (ii) latex and/or pseudolatex; (b) at least one bonding composition; and (c) one or more compositions selected from the group consisting of a topcoat composition, a basecoat composition, and a color coat composition; wherein the least one latex and/or at least one pseudolatex comprises at least one aqueous polyurethane dispersion comprising a reaction product of:

a prepolymer according to the following formula:

wherein $R_1$ represents a dihydroxyl compound having a number average molecular weights of from about 700 to about 16,000, $R_2$ represents a hydrocarbon radical of an aliphatic or cycloaliphatic polyisocyanate, and $R_3$ represents a radical of a low molecular weight diol, n is from 0 to 5, and m is >1;

at least one chain extender according to the formula: $H_2N$—$R_4$—$NH_2$ wherein $R_4$ represents an alkylene or alkylene oxide radical not substituted with ionic or potentially ionic groups; and at least one chain extender according to the formula: $H_2N-R_5-NH_2$ wherein $R_5$ represents an alkylene radical substituted with ionic or potentially ionic groups.

15. The method of claim 12, wherein the bonding composition is only present along the outside edges of the nail.

16. A method of making up a fingernail, comprising applying a primer on the fingernail, the primer comprising (a) water and (b) at least one latex and/or at least one pseudolatex, applying a bonding composition only to the outside edge of the fingernail, and applying a color coat; wherein the least one latex and/or at least one pseudolatex comprises at least one aqueous polyurethane dispersion comprising a reaction product of:

a prepolymer according to the following formula:

wherein $R_1$ represents a dihydroxyl compound having a number average molecular weights of from about 700 to about 16,000, $R_2$ represents a hydrocarbon radical of an aliphatic or cycloaliphatic polyisocyanate, and $R_3$ represents a radical of a low molecular weight diol, n is from 0 to 5, and m is >1;

at least one chain extender according to the formula: $H_2N-R_4-NH_2$ wherein $R_4$ represents an alkylene or alkylene oxide radical not substituted with ionic or potentially ionic groups; and at least one chain extender according to the formula: $H_2N-R_5-NH_2$ wherein $R_5$ represents an alkylene radical substituted with ionic or potentially ionic groups.

* * * * *

UNITED STATES PATENT AND TRADEMARK OFFICE
CERTIFICATE OF CORRECTION

PATENT NO. : 9,597,272 B2
APPLICATION NO. : 14/649368
DATED : March 21, 2017
INVENTOR(S) : Chunhua Li et al.

It is certified that error appears in the above-identified patent and that said Letters Patent is hereby corrected as shown below:

In the Claims

Column 22, Line 4, "at lean" should read --at least--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*